United States Patent [19]
Coy et al.

[11] Patent Number: 5,410,019
[45] Date of Patent: Apr. 25, 1995

[54] THERAPEUTIC PEPTIDES

[75] Inventors: David H. Coy, New Orleans, La.; Jacques-Pierre Moreau, Upton, Mass.

[73] Assignee: The Administrators of the Tulane-Educational Fund, New Orleans, La.

[21] Appl. No.: 860,675

[22] Filed: Mar. 30, 1992

Related U.S. Application Data

[63] Continuation-in-part of Ser. No. 394,727, Aug. 16, 1989, abandoned, which is a continuation-in-part of Ser. No. 317,941, Mar. 2, 1989, abandoned, which is a continuation-in-part of Ser. No. 282,328, Dec. 9, 1988, Pat. No. 5,162,497, which is a continuation-in-part of Ser. No. 257,998, Oct. 14, 1988, abandoned, which is a continuation-in-part of Ser. No. 248,771, Sep. 23, 1988, abandoned, which is a continuation-in-part of Ser. No. 207,759, Jun. 16, 1988, abandoned, which is a continuation-in-part of Ser. No. 204,171, Jun. 8, 1988, abandoned, which is a continuation-in-part of Ser. No. 173,311, Mar. 25, 1988, abandoned, which is a continuation-in-part of Ser. No. 100,571, Sep. 24, 1987, abandoned.

[51] Int. Cl.$^6$ ............................. C07K 7/02; C07K 7/06
[52] U.S. Cl. ..................................... 530/323; 530/327; 530/328; 530/329; 530/330
[58] Field of Search ............... 530/323, 327, 328, 329, 530/330

[56] References Cited

U.S. PATENT DOCUMENTS

| | | | |
|---|---|---|---|
| 4,207,311 | 6/1980 | Brown et al. | 424/177 |
| 4,481,139 | 11/1984 | Folkers et al. | 530/327 |
| 4,501,735 | 2/1985 | Hörig et al. | 514/17 |
| 4,737,487 | 4/1988 | Watts et al. | 514/15 |
| 4,803,261 | 2/1989 | Coy et al. | 530/333 |

FOREIGN PATENT DOCUMENTS

| | | |
|---|---|---|
| 0345990 | 12/1989 | European Pat. Off. |
| W002745 | 3/1991 | WIPO |

OTHER PUBLICATIONS

Cram et al., Organic Chemistry, 2nd Ed. McGraw-Hill Book Company, New York, pp. 607–613 (1964).
Rudingerm, Peptide Hormones, Parsons (Ed) U Park Press, Baltimore, pp. 1–7 (1976).
Coy et al., Tetrahedron, vol. 44, No. 3, pp. 835–841 (1988).
Jensen et al., J. of Physiol. vol. 254: G833 (1988).
Woll et al., "Proc. Natl. Acad. Sci. USA [D-Arg$^1$, D-Phe$^5$, D-Trp$^{7-9}$] Substance P apatent Bombes-n Antagonist in Murine Swiss 3T3 Cells, Inhibits Growth of Human SCLC Cells in vitro," 85:1859 (1988).
Payan, Ann. Rev. Med., "Neuropeptides and Inflammation: The Role of Substance P", 40:341 (1989).
Iverson et al., "The Tachykinin System," Abstract, 11th American Peptide Symposium, (1989).
Tourwe, Janssen Chem. Acta, "The Synthesis of Peptide Analogues with a Modified Peptide Bond", 3:3–15, 17–18 (1985).
Spatola, "Peptide Backbone Modifications," in Chemistry and Biochemistry of Amino Acids, Peptides, and Proteins, B., Weinstein, ed., M. Dekkee, New York, and Basel, pp. 267–357 (1983).
Caranikas et al., J. Med. Chem., "Synthesis and Biological Activities of Substance P Antagonists" 25:1313–1316 (1982).
Rosell et al., T.I.P.S., "Substance P Antagonists: A (List continued on next page.)

Primary Examiner—Christina Y. Chan
Attorney, Agent, or Firm—Fish & Richardson

[57] ABSTRACT

A linear peptide which is an analog of naturally occurring, biologically active substance P having an active site and a binding site responsible for the binding of the peptide to a receptor on a target cell. The analog has a non-peptide bond instead of a peptide bond between an amino acid residue of the active site and an adjacent amino acid residue, or a synthetic, a $\beta$-amino acid, or a $\alpha$-amino acid residue replacing two amino acid residues of the active site.

9 Claims, 4 Drawing Sheets

OTHER PUBLICATIONS

New Type of Pharmacological Tool," 3:211–212 (1982).

Lundberg et al., Proc. Natl. Acad. Sci. USA, "A Substance P Antagonist Inhibits vagally induced increase in vascular permeability and bronchial smooth muscle contra-tion in the guinea pig" 80:1120–1124 (1983).

Engberg et al., Nature, "A Synthetic Peptide as an Antagonist of Substance P" 293:222–223 (1981).

Mizrahi et al., Eur. J. Pharm., Substance P Antagonists Active in Vitro and In Vivo 82:101–105 (1982).

Leander et al., Nature, "A Specific Substance P Antagonist Blocks Smooth Muscle Constrations Induced by Non-Cholinergic non-adrenergic nerve Stimulation" 294-467–469 (1981).

Zhang et al., B.B.A., An Analog of Substance P with Broad Receptor Antagonist Acitivty, 972:37–44 (1988).

Zachary et al., Proc. Natl., Acad. Sci. USA, "High-affinity Receptors for Peptides of the Bombesin Family in Swiss 3T3 Cells," 82:7616–7620.

Coy et al., Tetrahedron, "Solid Phase Reductive Alkylation Techniques in Analogue Peptide Bond and Side Chain Modification" 44:835–841, 1988.

Coy et al., "Progress in the Develipment of of Competitive Bombesin Antagonist", in Abstract of the Intl. Sym. on Bombesin–like Peptides in Health and Disease, Rome, p. 105 (10.87).

Dubreuil et al., "Degradation of the tetragastrin analogue by a membrane fraction from rat gastric mucosa," Drug Design and Delivery 2:49–54, 1987.

Sawyer et al., J. Med. Chem. Design, Stucture-Activity, and Molecular Modeling Studies of Patent Renin Inhibitory Peptides having N-terminal Nin for Trp (FTR) 31:18–30, 1988.

Spatola et al., Tetrahedron, Amide Bond Surrogates: Pseudopeptides and Macrocycles 44:821–833, 1988.

Qian et al., The Journal of Biological Chemistry, vol. 264 pp. 16667–16671 (1989).

Zacharia et al., European Journal of Pharmacology, vol. 203 pp. 353–357 (1991).

Ewenson et al., J. Med. Chem. vol. 31, pp. 416–421 (1988).

Dutta et al., Journal of Med. Chem. vol. 29, No. 7, pp. 1171–1178 (1986).

Lehninger, Principles of Biochemistry, Worth Publishers, Inc., Anderson et al. (Ed.), New York, pp. 95–117 (1982).

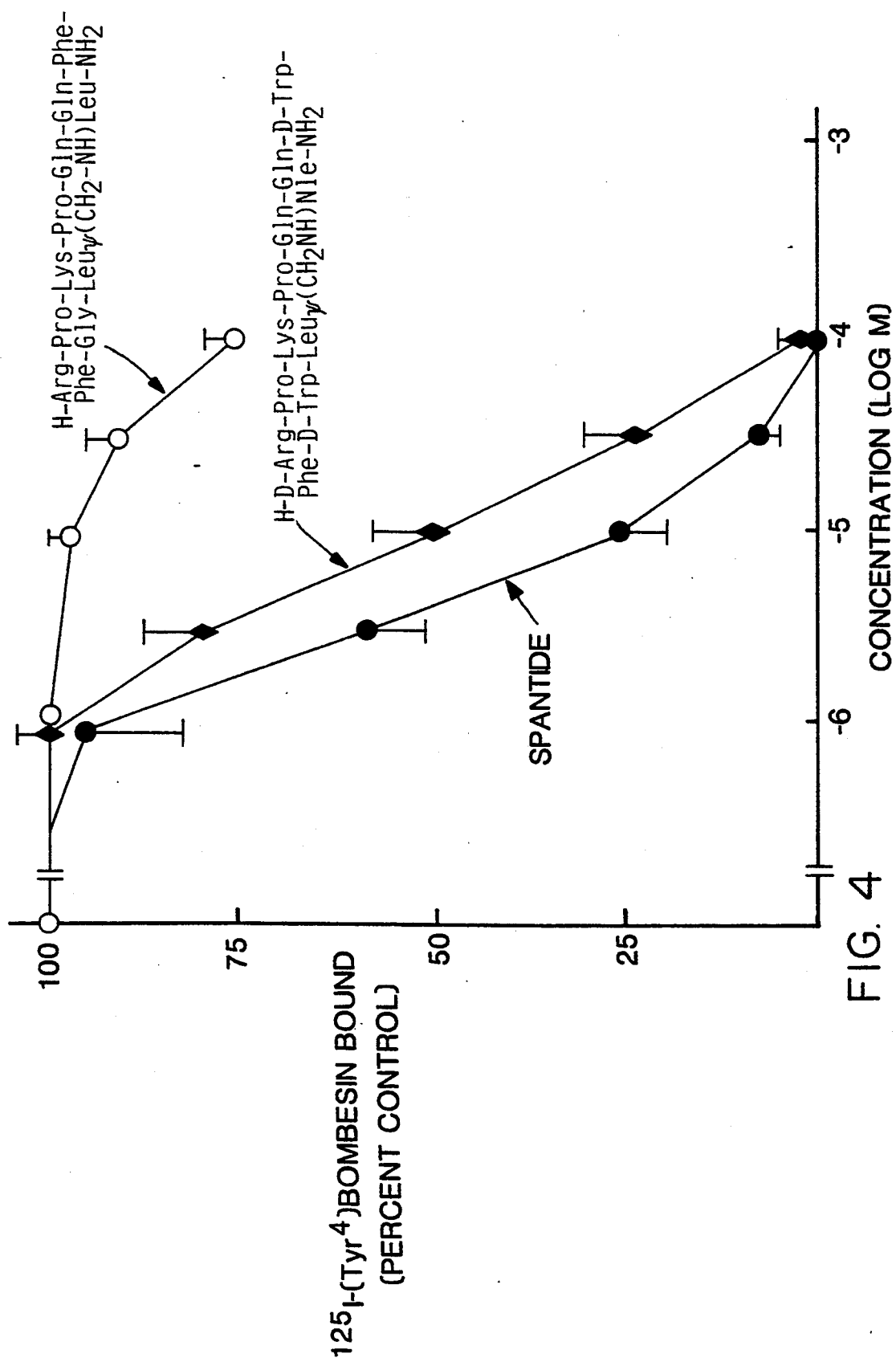

THERAPEUTIC PEPTIDES

BACKGROUND OF THE INVENTION

Applicants hereby request priority under 35 U.S.C. § 120. This application is a continuation-in-part of Coy et al., U.S. patent application Ser. No. 394,727, filed Aug. 16, 1989, abandoned which is a continuation-in-part of Coy et al., U.S. patent application Ser. No. 317,941, filed Mar. 2, 1989, now abandoned, which is a continuation-in-part of Coy et al., U.S. patent application Ser. No. 282,328, filed Dec. 9, 1988, now U.S. Pat. No. 5,162,497, which in turn is a continuation-in-part of Coy et al., U.S. patent application Ser. No. 257,998, filed Oct. 14, 1988, now abandoned, which in turn is a continuation-in-part of Coy et al., U.S. patent application Ser. No. 248,771, filed Sep. 23, 1988, now abandoned, which in turn is a continuation-in-part of Coy et al., U.S. patent application Ser. No. 207,759, filed Jun. 16, 1988, now abandoned, which in turn is a continuation-in-part of Coy et al., U.S. patent application Ser. No. 204,171, filed Jun. 8, 1988, now abandoned, which in turn is a continuation-in-part of Coy et al., U.S. patent application Ser. No. 173,311, filed Mar. 25, 1988, now abandoned, which in turn is a continuation-in-part of Coy et al., U.S. patent application Ser. No. 100,571, filed Sep. 24, 1987, now abandoned.

This invention relates to therapeutic peptides, in particular analogs of the naturally occurring peptide substance P.

Substance P (SP) has numerous pharmacologic effects including vasodilation and hypotension, contraction of non-vascular smooth muscle, stimulation of salivary and pancreatic secretion, depolarization of various neurons and histamine release from mast cells. SP is thought to play a variety of physiological roles (many of which are associated with the induction of pain). These include regulation of peristalsis and smooth muscle activity in the gastrointestinal tract, regulation of salivary and pancreatic secretion, regulation of the inflammatory response to peripheral tissue injury, neurotransmission, and regulation of neuro-immunomodulation. Mantyh et al. (1989) Proc. Natl. Acad. Sci. USA 86:5193 reports the presence of substance P receptors at wound sites in the central nervous system and suggests that SP may be involved in regulating the response to injury in the central nervous system as well as in peripheral tissues. Substance P is also a proliferative agent, stimulating the proliferation of fibroblasts, T-lymphocytes, endothelial cells, smooth muscle cells and astrocytes.

SP belongs to a family of bioactive peptides known as the tachykinins. The structure, activity, and function of SP and other tachykinins are discussed in Payan (1989) Ann. Rev. Med. 40:341. As discussed in Payan, SP shares common pharmacological properties and a conserved carboxyl terminal sequence (Phe-X-Gly-Leu-Met-NH$_2$, where X is a branched aliphatic or aromatic amino acid residue) with the other tachykinins. The principle biological activities, and the ability to bind to a receptor, reside in the carboxyl terminal sequence of these peptides. Selectivity toward a specific tachykinin receptor is determined by the amino-terminal sequence of the peptides Iverson et al., (1989) The Tachykinin System, Abstract presented at the 11th American Peptide Symposium. The conservation of carboxyl terminal sequence extends beyond SP and other mammalian tachykinins to other bioactive peptides, as shown in Table 1.

Numerous derivatives of SP, made by side chain modification and/or D-amino acid substitution, have been shown to act as SP receptor antagonists. Folkers, U.S. Pat. No. 4,481,139, describes substance P antagonists made by D or L amino acid substitution. These antagonists include the undecapeptide analog spantide (H-D-Arg-Pro-Lys-Pro-Gln-Gln-D-Trp-Phe-D-Trp-Leu-Leu-NH$_2$) as well as truncated analogs of substance P. Jensen et al. (1988) Am. J. of Physiol. 254:G883 characterized the ability of various SP antagonists to inhibit the action of bombesin. Jensen et al. studied four SP analogues: H-Arg-D-Pro-Lys-Pro-Gln-Gln-D-Phe-Phe-D-Trp-Leu-Met-NH$_2$; H-Arg-D-Pro-Lys-Pro-Gln-Gln-D-Trp-Phe-D-Trp-Leu-Met-NH$_2$; H-D-Arg-D-Pro-Lys-Pro-Gln-Gln-D-Trp-Phe-D-Trp-Leu-Leu-NH$_2$; and H-D-Arg-Pro-Lys-Pro-Gln-Gln-D-Trp-Phe-D-Trp-Leu-Leu-NH$_2$. Jensen et al. also studied two SP analogues with the first 3 amino acid residues deleted, H-D-Pro-Gln-Gln-D-Trp-Phe-D-Trp-Leu-Met-NH$_2$ and H-D-Pro-Gln-Gln-D-Trp-Phe-D-Trp-D-Trp-Met-NH$_2$. None of these receptor binding peptides are, however, specific to the SP receptor. All were found to inhibit bombesin-stimulated amylase release. Jensen et al. concluded that "the ability to inhibit the action of bombesin is a general property of SP analogues that also function as SP receptor antagonists and that the SP receptor antagonists are each inhibiting the action of bombesin by functioning as bombesin receptor antagonists."

Woll et al. (1988) Proc. Nat. Acad. Sci. USA 85:1857 found the substance P antagonist H-D-Arg-Pro-Lys-Pro-D-Phe-Gln-D-Trp-Phe-D-Trp-Leu-Leu-NH$_2$ a potent bombesin antagonist in murine Swiss 3T3 cells.

Agonists and antagonists of a wide spectrum of biologically active peptide hormones, including substance P, have been synthesized by the introduction of modification of the peptide bonds of the peptide hormone, see Spatola (1983) in Chemistry and Biochemistry of Amino Acids, Peptides, and Proteins (B. Weinstein, ed.) M. Dekker, New York and Basel, pp. 267–357, for a recent review of the field.

Abbreviations (uncommon):

cyclohexyl-Ala = (cyclohexyl alanine)

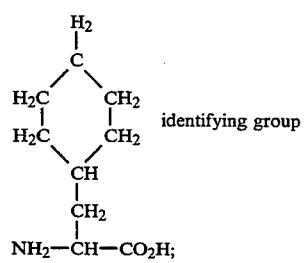

identifying group

Lys-ε-NHR = lysine wherein the ε-N atom carries an R group, R being any of H, $C_{1-12}$ alkyl, $C_{7-10}$ phenylalkyl, or COE where CO is a carbonyl group and E, attached to C of CO, is $C_{1-20}$ alkyl, $C_{3-20}$ alkenyl, $C_{3-20}$ alkynyl, phenyl, naphthyl, or $C_{7-10}$ phenylalkyl. (The symbol "COE" or the like is used to denote the same structure hereinafter.)

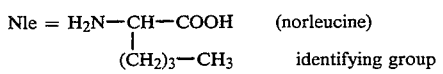 (norleucine) identifying group

Nal = naphthylalanine

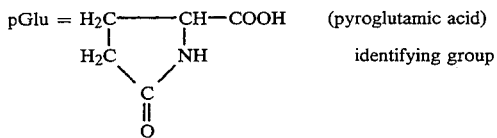 (pyroglutamic acid) identifying group

Sar = sarcosine
Sta (statine) =
(3S, 4S)-4-amino-3-hydroxy-6-methylheptanoic acid, and has the chemical structure:

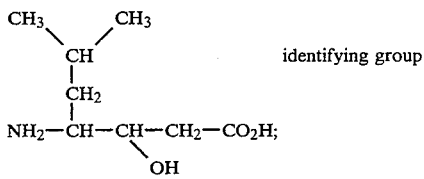 identifying group

AHPPA =
(3S,4S)-4-amino-3-hydroxy-5-phenylpentanoic acid, and has the chemical structure:

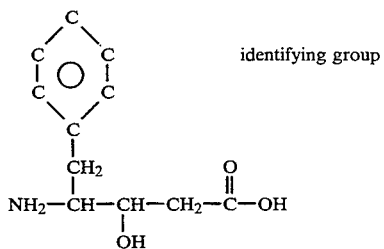 identifying group

ACHPA =
(3S, 4S)-4-amino-5-cyclohexyl-3-hydroxypentanoic acid and has the chemical structure:

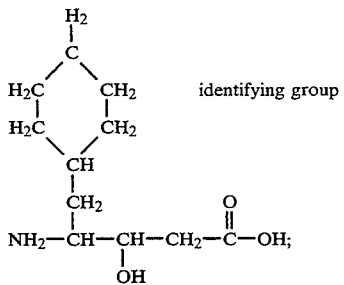 identifying group

Cpa = Chloro-Phenylalanine
SP = H-Arg-Pro-Lys-Pro-Gln-Gln-Phe-Phe-Gly-Leu-Met-NH$_2$ (substance P).

SUMMARY OF THE INVENTION

In general, the invention features a linear (i.e., non-cyclic) peptide which is an analog of a naturally occurring, biologically active peptide having an active site and a binding site responsible for the binding of the peptide to a receptor on a target cell; cleavage of a peptide bond in the active site of the naturally occurring peptide is unnecessary for in vivo biological activity.

The analog has one of the following modifications: (a) a non-peptide bond instead of a peptide bond between an amino acid residue of the active site and an adjacent amino acid residue, (b) a replacement of two amino acid residues within the active site with a synthetic amino acid residue, e.g., statine, AHPPA, ACHPA, a β-amino acid residue, or a γ-amino acid residue, (c) a deletion of an amino acid residue within the active site and a modification of an amino acid residue outside of the active site, or (d) the presence of an N-terminal amino acid residue that is not the naturally occurring amino acid residue of said naturally occurring, biologically active peptide (where β- or γ- is not designated an amino acid is an α-amino acid).

In preferred embodiments the analog is capable of acting as a competitive inhibitor of the naturally occurring peptide by binding to the receptor and, by virtue of one of the modifications, failing to exhibit the in vivo biological activity of the naturally occurring peptide.

In preferred embodiments the active site of the linear peptide is in the carboxyl terminal-half of the linear peptide. The linear peptide has one of the following modifications: (a) a non-peptide bond instead of a peptide bond between an amino acid residue of the active site and an adjacent amino acid residue, (b) a replacement of two amino acid residues within the active site with a synthetic amino acid residue, e.g., statine, AHPPA, ACHPA, a β-amino acid residue, or a γ-amino acid residue, (c) a deletion of an amino acid residue within the active site and a modification of an amino acid residue outside of the active site, or (d) the presence of an N-terminal amino acid residue that is not the naturally occurring amino acid residue of said naturally occurring, biologically active peptide.

In preferred embodiments the active site of the linear peptide is in the carboxyl terminal-half of the linear peptide. The linear peptide has one of the following modifications, (a) a non-peptide bond instead of a peptide bond between the carboxyl terminal amino acid residue and the adjacent amino acid residue, or (b) a statine or AHPPA or ACHPA, β-amino acid, or γ-amino acid residue in place of the naturally occurring carboxyl terminal and adjacent amino acid residues.

In preferred embodiments the linear peptide is an analog of naturally occurring biologically active substance P. The analog of substance P has one of the following modifications, (a) a non-peptide bond instead of a peptide bond between the carboxyl terminal amino acid residue and the adjacent amino acid residue, or (b) a statine or AHPPA or ACHPA, β-amino acid, or γ-amino acid residue in place of the naturally occurring carboxyl terminal and adjacent amino acid residues.

In preferred embodiments the analog of substance P is capable of acting as a competitive inhibitor of the naturally occurring substance P by binding to the receptor and, by virtue of one of the modifications, failing to exhibit the in vivo biological activity of the naturally occurring peptide.

In preferred embodiments the linear peptide is an analog of substance P with an active site in the carboxyl terminal-half of the linear peptide. The analog of substance P has one of the following modifications: (a) a non-peptide bond instead of a peptide bond between the carboxyl terminal amino acid residue and the adjacent amino acid residue, or (b) a statine or AHPPA or ACHPA or β-amino acid or γ-amino acid residue in place of the naturally occurring carboxyl terminal and adjacent amino acid residues.

The linear peptides for which introduction of a non-peptide bond between two amino acid residues, or the replacement of two natural amino acid residues with a synthetic amino acid residue, a β-amino acid residue, or a γ-amino acid residue, or the deletion ("des") of the C-terminal amino acid residue useful in creating or enhancing antagonist activity are those in which activity is associated with the two C-terminal amino acid residues of the amino acid chain. Therefore, the active site of the naturally occurring peptide of which the peptides of the invention are analogs preferably includes at least on amino acid residue in the carboxy terminal half of the peptide, and the linear peptide of the invention includes that amino acid residue in its carboxy terminal half. Modifications can be introduced in a region involved in receptor binding, or in a non-binding region.

By non-peptide bond is meant that the carbon atom participating in the bond between two residues is reduced from a carbonyl carbon to a methylene carbon, i.e., $CH_2$—NH; or $CH_2$—S, $CH_2$—O, $CH_2$—$CH_2$, $CH_2$—CO, or CO—$CH_2$. (A detailed discussion of the chemistry of non-peptide bonds is given in Coy et al. (1988) Tetrahedron 44,3:835-841, hereby incorporated by reference, Tourwe (1985) Janssen Chim. Acta 3:3-15, 17-18, hereby incorporated by reference, and Spatola (1983) in Chemistry and Biochemistry of Amino Acids, Peptides, and Proteins, (B. Weinstein, ed.) M. Dekker, New York and Basel, pp. 267-357, hereby incorporated by reference.)

Preferably, analogs of the invention are 25% homologous, most preferably, 50% homologous, with the naturally occurring peptides.

One modification of the naturally occurring peptide to create an antagonist is to employ, as the amino terminal residue, an aromatic D-isomer of an amino acid, or an alkylated amino acid. (Where "D" is not designated as the configuration of an amino acid, L is intended.)

One class of peptide of the invention includes the substance P analogs of the formula:

or p-X-Phe in which X is F, Cl, Br, $NO_2$, OH, or $CH_3$; or is deleted;

$A^6$ = the D or L isomer of Ala, Arg, Ser, Pro, Gln, pGlu, Asn, β-Nal, Trp, Phe, o-X-Phe in which X is F, Cl, Br, $NO_2$, OH, or $CH_3$, or p-X-Phe in which X is F, Cl, Br, $NO_2$, OH, or $CH_3$;

$A^7$ = the D or L isomer of Val, Thr, Phe, Trp, βNal, o-X-Phe in which X is F, Cl, Br, $NO_2$, OH, or $CH_3$, or p-X-Phe in which X is F, Cl, Br, $NO_2$, OH, or $CH_3$;

$A^8$ = the identifying group of Gly or the D or L isomer of Val, Trp, β-Nal, Phe, o-X-Phe in which X is F, Cl, Br, $NO_2$, OH, or $CH_3$, or p-X-Phe in which X is F, Cl, Br, $NO_2$, OH, or $CH_3$;

$A^9$ = Gly or the D or L isomer of Sar, His, Trp, β-Nal, Phe, o-X-Phe in which X is F, Cl, Br, $NO_2$, OH, or $CH_3$, or p-X-Phe in which X is F, Cl, Br, $NO_2$, OH, or $CH_3$;

$A^{10}$ = Gly or the identifying group of the D or L isomer of Trp, β-Nal, Leu, Nle, Ala, cyclohexyl-Ala, Val, Ile, Met, Phe, o-X-Phe in which X is, Cl, Br, $NO_2$, OH, or $CH_3$, or p-X-Phe in which X is F, Cl, Br, $NO_2$, OH, or $CH_3$;

$A^{11}$ = Gly or the identifying group of the D or L isomer of Trp, β-Nal, Leu, Nle, Ala, Val, Ile, Met, Phe, o-X-Phe in which X is F, Cl, Br, $NO_2$, OH, or $CH_3$, or p-X-Phe in which X is F, Cl, Br, $NO_2$, OH, or $CH_3$; or is deleted;

$R_5$ is any one of $CH_2$-NH, $CH_2$-S, $CH_2$-O, $CH_2$-$CH_2$, $CH_2$-CO, or CO—$CH_2$; $R_6$ is C; and $V^1$ is

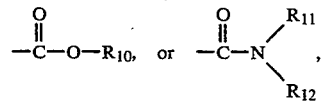

in which each $R_{10}$, $R_{11}$, and $R_{12}$ independently, is H, $C_{1-12}$ alkyl, $C_{7-10}$ phenylalkyl, or $C_{12-20}$ naphthylalkyl; further provided that, where $A^5$ is Asp, A is Ser, $A^6$ is Phe, $A^8$ is Val, $A^9$ is Gly, $A^{10}$, $A^{11}$ is Leu is Leu, and $R_5$ is $CH_2NH$, at least one of $A^1$, $A^2$, $A^3$, or $A^4$, must be present; or said analog with one or both of the hydro-

wherein $A^1$ = the D or L isomer of Arg, Lys, or Lys-ε-NH-$R_{20}$ in which $R_{20}$ is any of H, $C_{1-12}$ alkyl, $C_{7-10}$ phenylalkyl, $C_{1-12}$ acyl, or $COE_{10}$ with $E_{10}$ being $C_{1-20}$ alkyl, $C_{3-20}$ alkenyl, $C_{3-20}$ alkynyl, phenyl, naphthyl, or $C_{7-10}$ phenylalkyl; or is deleted; the D or L isomer Pro; or is deleted;

$A^3$ = the D or L isomer of Lys, or Lys-ε-NH-$R_{22}$ in which $R_{22}$ is any of H, $C_{1-12}$ alkyl, $C_{7-10}$ phenylalkyl, $C_{1-12}$ acyl, or $COE_{12}$ with $E_{12}$ being $C_{1-20}$ alkyl, $C_{3-20}$ alkenyl, $C_{3-20}$ alkynyl, phenyl, naphthyl, or $C_{7-10}$ phenylalkyl; or is deleted;

$A^4$ = the D or L isomer of Pro; or is deleted;

$A^5$ = the D or L isomer of Asp, Gln, β-Nal, Trp, Phe, o-X-Phe in which X is F, Cl, Br, $NO_2$, OH, or $CH_3$, gens of its α-amino group at the N-terminus replaced by one or both of $R1$ and $R_2$, $R_1$, and $R_2$, independently, being $C_{1-12}$ alkyl, $C_{7-10}$ phenylalkyl, or $COE_{14}$ with $E_{14}$ being $C_{1-20}$ alkyl, $C_{3-20}$ alkenyl, $C_{3-20}$ alkynyl, phenyl, naphthyl, or $C_{7-10}$ phenylalkyl, provided that when one of $R_1$ or $R_2$ is $COE_{14}$, only one of said hydrogens is replaced by $R_1$ or $R_2$; or a pharmaceutically acceptable salt thereof.

Note that amino acid residues, such as Ser, Arg, Leu, and the like, stand for the structure NH-CH(I)-CO, where I is the identifying group of an amino acid. For example, I is $CH_2OH$ for Ser. However, for pyroglutamate, see below.

Another class of peptide of the invention includes the substance P analogs of the formula:

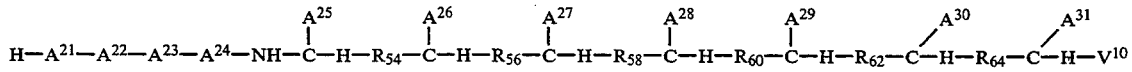

wherein $A^{21}$ = the D or L isomer of Arg, Lys, or Lys-ε-NH-$R_{80}$ in which $R_{80}$ is any of H, $C_{1-12}$ alkyl, $C_{7-10}$ phenylalkyl, $C_1$-$C_{12}$ acyl, or $COE_{20}$ with $E_{20}$ being $C_{1-20}$ alkyl, $C_{3-20}$ alkenyl, $C_{3-20}$ alkynyl, phenyl, naphthyl, or $C_{7-10}$ phenylalkyl; or is deleted;

$A^{22}$ = the D or L isomer of Pro; or is deleted;

$A^{23}$ = the D or L isomer of Lys or Lys-ε-NH-$R_{82}$ in which $R_{82}$ is any of H, $C_{1-12}$ alkyl, $C_{7-10}$ phenylalkyl, $C_1$-$C_{12}$ acyl, or $COE_{22}$ with $E_{22}$ being $C_{1-20}$ alkyl, $C_{3-20}$ alkenyl, $C_{3-20}$ alkynyl, phenyl, naphthyl, or $C_{7-10}$ phenylalkyl; or is deleted;

$A^{24}$ = the D or L isomer of Pro; or is deleted;

$A^{25}$ = the identifying group of the D or L isomer of Asp, Gln, β-Nal, Trp, Phe, o-X-Phe in which X is F, Cl, Br, $NO_2$, OH, or $CH_3$, or p-X-Phe in which X is F, Cl, Br, $NO_2$, OH, or $CH_3$; or is deleted together with NH—CH—$R_{54}$ bonded thereto;

$A^{26}$ = the identifying group of the D or L isomer of Arg, Sar, Pro, Gln, pGlu, Phe, Trp, cyclohexyl-Ala, or Asn;

$A^{27}$ = the identifying group of D-Trp; or the identifying group of the D or L isomer of Leu, Phe, or cyclohexyl-Ala;

$A^{28}$ = the identifying group of the D or L isomer of any one of the amino acids Val, β-Nal, Phe, o-X-Phe in which X is F, Cl, Br, $NO_2$, OH, or $CH_3$, or p-X-Phe in which X is F, Cl, Br, $NO_2$, OH, or $CH_3$;

$A^{29}$ = the identifying group of the amino acid D-Trp; or the identifying group of the D or L isomer of any of Leu, Phe, or cyclohexyl-Ala;

$A^{30}$ = the identifying group of the D or L isomer of any one of the amino acids Leu, Nle, Ala, cyclohexyl-Ala, Ala, Val, Ile, Met, Gly, Phe, Trp, β-Nal, o-X-Phe in which X is F, Cl, Br, $NO_2$, OH, or $CH_3$, or p-X-Phe in which X is F, Cl, Br, $NO_2$, OH, or $CH_3$;

$A^{31}$ = the identifying group of the D or L isomer of any one of the amino acids Trp, β-Nal, Leu, Nle, Ala, Val, Ile, Met, Gly, Phe, o-X-Phe in which X is F, Cl, Br, $NO_2$, OH, or $CH_3$, or p-X-Phe in which X is F, Cl, Br, $NO_2$, OH, or $CH_3$;

$R_{54}$ is CO—NH or CO—$NCH_3$ if $A^{25}$ with NH—CH—$R_{54}$ is not deleted, is NH if $A^{25}$ with NH—CH—$R_{54}$ is deleted; each $R_{56}$, $R_{62}$, and $R_{64}$, independently, is any of CO—NH, $CH_2$—NH, $CH_2$—S, $CH_2$—O, $CH_2CH_2$—$CH_2$, $CH_2$—CO, or CO—$CH_2$; $R_{58}$ is CO—$NR_{69}$ in which $R_{69}$ is H or $C_{1-12}$ alkyl, $CH_2$—NH, $CH_2$—S, $CH_2$—O, $CH_2$—$CH_2$, $CH_2$—CO, or CO—$CH_2$; $R_{60}$ is CO—NH; and $V^{10}$ is

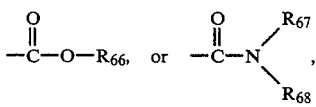

in which each $R_{66}$, $R_{67}$, and $R_{68}$ independently, is H, $C_{1-12}$ alkyl, $C_{7-10}$ phenylalkyl, or $C_{12-20}$ naphthylalkyl; provided that, at least one of $R_{56}$, $R_{58}$, $R_{62}$, or $R_{64}$ is other than either CO—NH or CO—$NR_{69}$; or said analog with one or both of the hydrogens of its α-amino group at the N-terminus replaced by one or both of $R_{51}$ and $R_{52}$, $R_{51}$ and $R_{52}$, independently, being $C_{1-12}$ alkyl, $C_{7-10}$ phenylalkyl, or $COE_{24}$ with $E_{24}$ being $C_1$-$C_{20}$ alkyl, $C_{3-20}$ alkenyl, $C_{3-20}$ alkynyl, phenyl, naphthyl, or $C_{7-10}$ phenylalkyl, provided that when one of $R_{51}$ or $R_{52}$ is $COE_{24}$, only one of said hydrogens is replaced by $R_{51}$ or $R_{52}$; or a pharmaceutically acceptable salt thereof.

Examples of preferred peptides are:
H-Arg-Pro-Lys-Pro-Gln-Gln-Phe-Phe-Gly-Leuψ[C-H2—NH]Leu-$NH_2$; H-D-Arg-Pro-Lys-Pro-Gln-Gln-D-Trp-Phe-D-Trpψ[$CH_2$—NH]Leu-Nle-$NH_2$; H-D-Arg-Pro-Lys-Pro-Gln-Gln-D-Trpψ[$CH_2$—NH]Phe-D-Trp-Leu-Nle-$NH_2$; H-D-Arg-Pro-Lys-Pro-Gln-Glnψ[$CH_2$—NH]D-Trp-Phe-D-Trp-Leu-Nle-$NH_2$ or H-D-Arg-Pro-Lys-Pro-Gln-Gln-D-Trp-Phe-D-Trp-Leuψ[$CH_2$—NH]Nle-$NH_2$. (Non-peptide bonds in which the peptide bond are symbolized herein by "ψ[$CH_2$—NH]", "Ψ[$CH_2$O]" or the like, depending on the types of modification on the peptide bond].

In another aspect the invention features a substance P agonist/antagonist of the formula:
H-Arg-Pro-Lys-Pro-Gln-Gln-Phe-Phe-Gly-Leuψ[C-H2—NH]Leu-$NH_2$; H-Arg-Pro-Lys-Pro-Gln-Gln-Pheψ[$CH_2$—NH]Phe-Gly-Leu-Leu-$NH_2$; H-Arg-Pro-Lys-Pro-Gln-Gln-Phe-Phe-Gly-Leuψ[$CH_2$—O]Leu-$NH_2$; H-Arg-Pro-Lys-Pro-Gln-Gln-Phe-Phe-Glyψ[C-H2—NH]Leu-Leu-$NH_2$; H-D-Phe-Gln-Phe-Phe-Gly-Leuψ[$CH_2$—O]Leu-$NH_2$; H-D-Phe-Gln-Phe-Gly-Leuψ[$CH_2$—NH]Phe-$NH_2$; H-D-Nal-Gln-Phe-Phe-Gly-Leuψ[$CH_2$—NH]Phe-$NH_2$; H-D-Cpa-Gln-Phe-Phe-Gly-Leuψ[$CH_2$—NH]Phe-$NH_2$; or H-D-Phe-Phe-Gly-Leuψ[$CH_2$-NH]Leu-$NH_2$.

All these analogs have been shown to possess agonist or antagonist activity on biosystems such as the guinea pig ileum and/or the rat duodenum.

SP antagonists of the invention are useful in the treatment of a patient suffering from diseases involving neurogenic inflammation e.g., rheumatoid arthritis, ulcerative colitis, eczema, and Crohn's disease. The SP antagonists of the invention are useful as antiproliferative agents e.g., in the treatment of small cell lung carcinoma or disorders involving the proliferation of fibroblasts. The antiproliferative properties of the SP antagonists of the invention also allow their use in the prevention of glial scarring (thus facilitating nerve regeneration). The action of the antagonists of the invention on neurotransmission allow their use as nonopiate analgesics. Their use as nonopiate analgesics can permit the restoration of opiate response. The antagonists of the invention are also useful as antisecretory agents, acting e.g., on the salivary glands or on the pancreas.

In the generic formulas given above, when any of $R_1$, $R_2$, $R_7$-$R_{13}$, $R_{51}$, $R_{52}$, $R_{66-R68}$, or $R_{70-R72}$ is an aromatic, lipophilic group, the in vivo activity can be long lasting, and delivery of the compounds of the invention to the target tissue can be facilitated.

The identifying group of an α-amino acid (for case of pyroglutamate, see below) is the atom or group of atoms, other than the α-carbonyl carbon atom, the α-amino nitrogen atom, or the H atom, bound to the asymmetric α-carbon atom. To illustrate by examples, the identifying group of alanine is $CH_3$, the identifying group of valine is $(CH_3)_2CH$, the identifying group of lysine is $H_3N^+$ $(CH_2)_4$ and the identifying group of phenylalanine is $(C_6H_6)CH_2$. The identifying group of a β- or γ-amino acid is the analogous atom or group of atoms bound to respectively, the β- or the γ-carbon atom. Where the identifying group of an amino acid is not specified, it may be a α, β, or γ. In the case of pyroglutamate the identifying group consists of —NH—CO—$CH_2$—$CH_2$—.

Other features and advantages of the invention will be apparent from the following description of the preferred embodiments thereof, and from the claims.

DESCRIPTION OF THE PREFERRED EMBODIMENTS

We first briefly describe the drawings. Drawings

FIG. 4 is a graph showing the ability of SP and spantide pseudopeptides to inhibit binding of $^{125}$I-[Tyr$^4$] bombesin to pancreatic acini.

Figure 1:
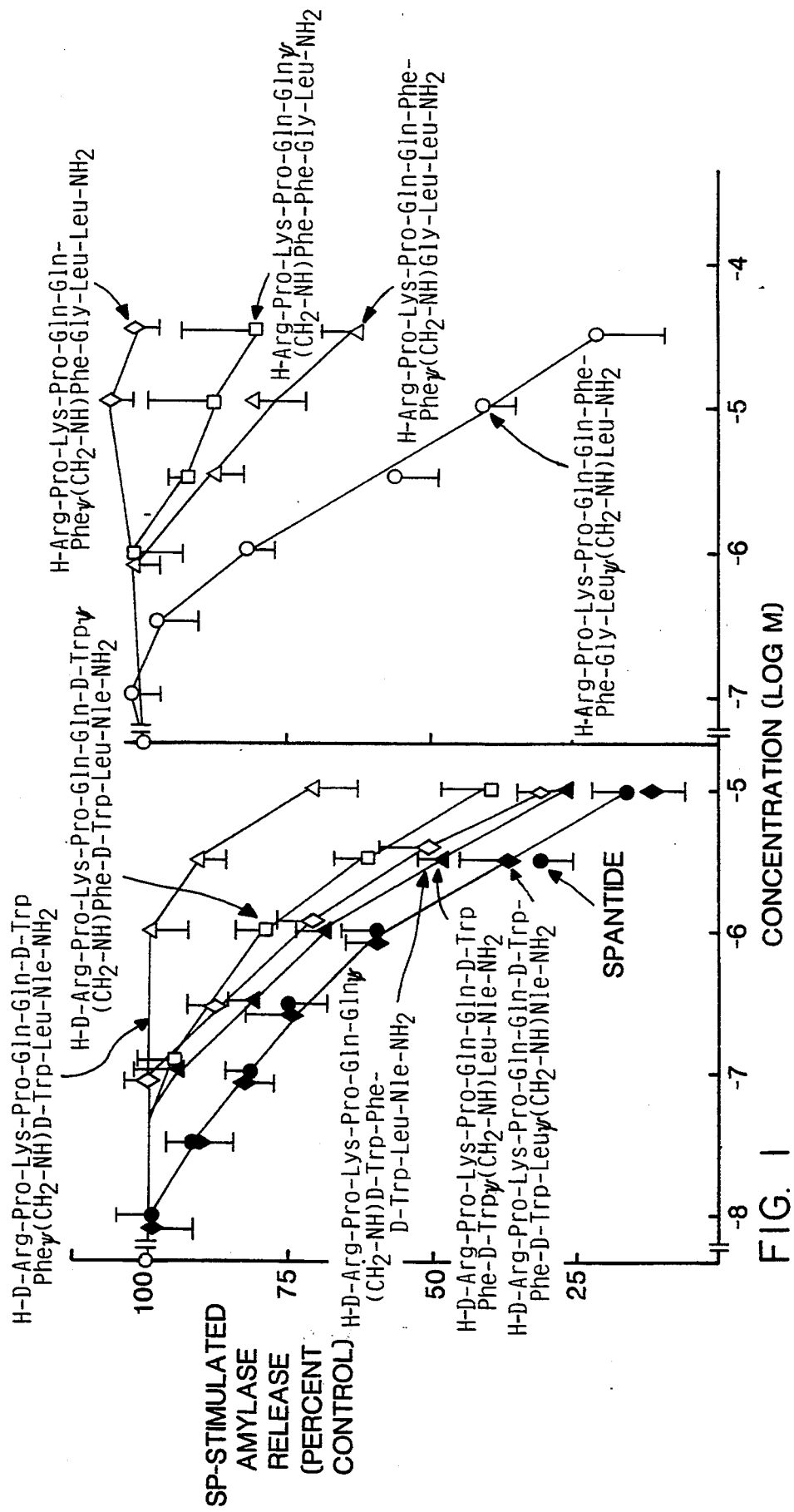
FIG. 1 is a pair of graphs illustrating the effect of pseudopeptides of spantide, H-D-Arg-Pro-Lys-Printer 08 (HP IID- 32 - Bay)P08.PRSPRSI panel) on SP-stimulated amylase release from pancreatic acini.

We now describe the structure, synthesis, and use of preferred embodiments of the invention.

Structure

The peptides of the invention all have modifications, e.g., a non-peptide bond in at least one of the indicated positions in which the carbon atom participating in the bond between two residues is reduced from a carbonyl carbon to a methylene carbon. The peptide bond reduction method which yields this non-peptide bond is described in Coy et al., U.S. patent application, Ser. No. 879,348, now U.S. Pat. No. 4,803,261, assigned to the same assignee as the present application, hereby incorporated by reference. The peptides of the invention can be provided in the form of pharmaceutically acceptable salts. Examples of preferred salts are those with therapeutically acceptable organic acids, e.g., acetic, lactic, maleic, citric, malic, ascorbic, succinic, benzoic, salicylic, methanesulfonic, toluenesulfonic, or pamoic acid, as well as polymeric acids such as tannic acid or carboxymethyl cellulose, and salts with inorganic acids such as the hydrohalic acids, e.g., hydrochloric acid, sulfuric acid, or phosphoric acid.

Synthesis of Substance P Analogs

Solid phase syntheses of peptides, including introduction of reduced peptide bond, were carried out by the automated methods recently described by Coy et al. J. Biol. Chem. 263:5056 (1988) and Sasaki et al. Peptides 8:119 (1987) employing Advanced ChemTech ACT 200 machines. Both articles are incorporated herein by reference.

The synthesis of the substance P antagonist H-Arg-Pro-Lys-Pro-Gln-Gln-Phe-Phe-Gly-Leu$\psi$[CH$_2$NH-]Leu-NH$_2$ follows. Other substance P analogs of the invention can be prepared by making the appropriate modifications of the following synthetic method. Such modifications are well known in the art.

The first step is the preparation of the intermediate H-Arg-Pro-Lys-Pro-Gln-Gln-Phe-Phe-Gly-Leu$\psi$[CH$_2$NH]Leu-benzhydrylamine resin, as follows.

Benzhydrylamine-polystyrene resin (Vega Biochemicals, Inc.) (0.97 g, 0.5 mmole) in the chloride ion form is placed in the reaction vessel of a BECKMAN 990B peptide synthesizer programmed to perform the following reaction cycle: (a) methylene chloride; (b) 33% trifluoroacetic acid (TFA) in methylene chloride (2 times for 1 and 25 min. each); (c) methylene chloride; (d) ethanol; (e) methylene chloride; and (f) 10% triethylamine in chloroform.

The neutralized resin is stirred with alpha-t-butoxycarbonyl(Boc)-leucine and diisopropylcarbodiimide (1.5 mmole each) in methylene chloride for 1 hour, and the resulting amino acid resin is then cycled through steps (a) to (f) in the above wash program. Boc-leucine aldehyde (1.25 mmoles), prepared by the method of Fehrentz and Castro, Synthesis, p. 676 (1983), is dissolved in 5 ml of dry dimethylformamide (DMF) and added to the resin TFA salt suspension followed by the addition of 100 mg (2 mmoles) of sodium cyanoborohydride (Sasaki and Coy, Peptides 8:119–121 (1987); Coy et al., id.) After stirring for 1 hour, the resin mixture is found to be negative to ninhydrin reaction (1 min.), indicating complete derivatization of the free amino group.

The following amino acids (1.5 mmole) are then coupled successively in the presence diisopropylcarbodiimide (1.5 mmole), and the resulting amino acid resin is cycled through washing/deblocking steps (a) to (f) in the same procedure as above: Boc-Gly (Boc-Gly is coupled as a 6M excess of the p-nitrophenylester), Boc-Phe, Boc-Phe, Boc-Gln, Boc-Gln, (Boc-Gln is coupled as a 6M excess of the p-nitrophenylester), Boc-Pro, Boc-Lys, Boc-Pro, and Boc-Arg. The completed resin is then washed with methanol and air dried.

The resin described above (1.6 g, 0.5 mmole) is mixed with anisole (5 ml) and anhydrous hydrogen fluoride (35 ml) at 0° C. and stirred for 45 min. Excess hydrogen fluoride is evaporated rapidly under a stream of dry nitrogen, and free peptide is precipitated and washed with ether. The crude peptide is dissolved in a minimum volume of 2M acetic acid and purified on a column (2.5×90 cm) of SEPHADEX G-25 which is eluted with 2M acetic acid, followed by preparative medium pressure chromatography on a column (1.5×45 cm) of VYDAC C$_{18}$ silica (10–15 $\mu$m) which is eluted with linear gradients of acetonitrile in 0.1% trifluoroacetic acid using an ELDEX CHROMATROL GRADIENT CONTROLLER (flow rate 1 ml/min). Where necessary, analogues are further purified by re-chromatography on the same column with slight modifications to the gradient conditions when necessary. Homogeneity of the peptides was assessed by thin layer chromatography and analytical reverse-phase high pressure liquid chromatography, and purity was 97% or higher. Amino acid analysis gave the expected amino acid ratios. The presence of the reduced peptide bond was demonstrated by fast atom bombardment mass spectrometry. Each of the analogues gave good recovery of the molecular ion corresponding to the calculated molecular mass.

A statine, AHPPA, ACHPA, $\beta$-amino acid, or $\gamma$-amino acid residue is added in the same way as is a natural $\alpha$-amino acid residue, by coupling as a Boc-amino acid. Statine or Boc-statine can be synthesized according to the method of Rich et al., 1978, J. Org. Chem. 43; 3624; Rich et al. (1988) J. Org. Chem. 53:869; and Rich et al., 1980, J. Med. Chem. 23:27. AHPPA can be synthesized according to the method of Hui et al., 1987, J. Med. Chem. 30:1287. ACHPA can be synthesized according to the method of Schuda et al., 1988, Journal of Organic Chemistry 53:873. Boc-coupled synthetic amino acids are available from Nova Biochemicals (Switzerland), Bachem (Torrance, Calif.), and CalBiochem (San Diego, Calif.).

Peptides containing the CH$_2$O peptide bond replacement were synthesized via carbodiimide/1-hydroxybenzotriazole-mediated incorporation of the Boc-Leu-Ψ(CH$_2$O)-Leu-OH pseudodipeptide unit which was purchased from Neosystem Laboratories, Strasbourg, France. The crude hydrogen fluoride-cleaved peptides were purified on a SEPHADEX G-25 column, eluted with 2M acetic acid, followed by preparative medium pressure chromatography on a VYDAC C18 silica column (10–15 μm), eluted with linear gradients of acetonitrile in 0.1% trifluoroacetic acid. When necessary, peptides were further purified by re-chromatography on the same column. Homogeneity of the peptides was assessed by thin layer chromatography and analytical reverse-phase high pressure liquid chromatography. The purity of peptides was at least 97%. The presence of the pseudopeptide bonds was demonstrated by fast atom bombardment mass spectrometry.

Other compounds can be prepared as above and tested for effectiveness as agonists or antagonists in the following test program.

Phase 1- Amylase Release From Pancreatic Acini

SP stimulates the release of amylase in pancreatic acini. The stimulation or inhibition of release of amylase by pancreatic acini is used as a measure of, respectively, the agonist or antagonist activity of a peptide. Dispersed acini from the pancreas of one animal are suspended in 150 ml of standard incubation solution. Amylase release is measured as described previously (Gardner et al. (1977) J. Physiol. 270:439). Amylase activity is determined by the methods of Ceska et al. (Ceska et al. (1969) Clin. Chim. Acta. 26:437 and Ceska et al. (1969) Clin. Chim. Acta. 26:445) using the PHADEBAS REAGENT. Amylase release is calculated as the percentage of the amylase activity in the acini at the beginning of the incubation that was released into the extracellular medium during the incubation.

Phase 2 - Competitive Inhibition of $^{125}$I-Bolton-Hunter-SP Binding

Binding of $^{125}$I-Bolton-Hunter-SP ($^{125}$I-BH-SP) to dispersed pancreatic acini is measured as described previously (Jensen et al. (1984) Biochem. Biophys. Acta. 804:181 and Jensen et al. (1988) Am. J. Physiol. 254:G883). Incubations contain 0.125 nM $^{125}$I-BH-SP and 0.1% bacitracin in standard incubation buffer and were for 30 min at 37° C. Nonsaturable binding of 125I-BH-SP is the amount of radioactivity associated with the acini when the incubation contains 0.125 nM $^{125}$I-BH-SP plus 1 μM unlabeled SP. All values given are for saturable binding, i.e., binding measured with $^{125}$I-BH-SP alone (total binding). In all experiments nonsaturable binding was <30% of total binding.

Phase 3 - Competitive Inhibition of $^{125}$I-[Tyr$^4$] Bombesin Binding $^{125}$I-[Tyr$^4$]0 Bombesin (2200 Ci/mmol) is prepared using a modification of the method described previously (Jensen et al. (1978) Proc. Natl. Acad. Sci. USA 75:6139). IODO-GEN (1 mg) is dissolved in 5 ml of chloroform and 5 μl of this solution (1 μg IODO-GEN) is transferred to a vial under a stream of nitrogen. To this vial 50 μl of KH$_2$PO$_4$ (pH 7.4) 6 μg [Tyr]bombesin in 5 μl water and 1 mCi , Na$^{125}$I is added mixed and incubated for 6 min at 4° C. at which time the iodination mixture is added to a vial of 1M dithiothreitol and incubated at 80° C. for 60 min. The iodination mixture is then loaded onto a SEP-PAK CARTRIDGE and eluted with 0.25M tetraethylammonium phosphate (TEAP) followed by 50% (vol/vol) acetonitrile-0.25M TEAP. $^{125}$I-[Tyr$^4$]bombesin is purified using reverse-phase high-performance liquid chromatography (HPLC) and eluted.

Results of Assays of Test Peptides

A number of analogues of substance P, or of the substance P antagonist spantide, each containing a non-peptide bond, can be synthesized and tested in one or more of the assays described in Phase 114 Phase 3 above. The structure of substance P is H-Arg-Pro-Lys-Pro-Gln-Gln-Phe-Phe-Gly-Leu-Met- NH$_2$. Spantide is an analog of SP. The structure of spantide is H-D-Arg-Pro-Lys-Pro-Gln-Gln-D-Trp-Phe-D-Trp-Leu-Leu-NH$_2$. Stimulation or inhibition of the release of amylase from dispersed pancreatic acini was used as an assay for SP agonist activity or SP antagonist activity respectively. At a concentration of 10 μM, 9 of 10 SP and spantide derived pseudopeptides failed to stimulate amylase release when present alone (Table 2). One peptide, H-Arg-Pro-Lys-Pro-Gln-Gln-Phe-Phe-GlyΨ[CH$_2$—NH]Leu-Leu-NH$_2$, (10 μM) had agonist activity causing a 3-fold increase in amylase release (Table 2). Each of the 9 pseudopeptides without agonist activity was examined for activity as a SP antagonist. At a concentration of 10μM each of the spantide derived pseudopeptide analogues inhibited 1 nM-SP-stimulated amylase release. (Table 2) Three SP pseudopeptides, H-Arg-Pro-Lys-Pro-Gln-Gln-Phe-Phe-Gly-LeuΨ[CH$_2$—NH]Leu-NH$_2$, H-Arg-Pro-Lys-Pro-Gln-Gln-Phe-PheΨ[CH$_2$—NH]Gly-Leu-Leu-NH2, and H-Arg-Pro-Lys-Pro-Gln-GlnΨ[CH$_2$-NH]Phe-Phe-Gly-Leu-Leu-NH$_2$ caused inhibition (Table 2).

The relative abilities of each peptide to inhibit SP-stimulated amylase release was determined by the effect of peptide dose on inhibition. Dose-inhibition studies were carried out for each of the 9 pseudopeptides using a concentration of SP (1 nM) that causes half-maximal stimulation. (FIG. 1). Results for the 5 spantide derived pseudopeptides are shown in FIG. 1, left panel. H-D-Arg-Pro-Lys-Pro-Gln-Gln- H-D-Trp-Phe-D-Trp-LeuΨ[CH$_2$—NH]Nle-NH$_2$ was equipotent to spantide, causing detectable inhibition at 0.03 μM and half-maximal inhibition at 1.8 μM (Table 3). H-D-Arg-Pro-Lys-Pro-Gln-Gln-D-Trp-Phe-D-TrpΨ[CH$_2$—NH]Leu-Nle-NH$_2$ was 2-fold less potent (IC$_{50}$3.5 μM, Table 3) than spantide. H-D-Arg-Pro-Lys-Pro-Gln-GlnΨ[CH$_2$—NH]D-Trp-Phe-D-Trp-Leu-Nle-NH$_2$ was 2.6-times (IC50 4.7 μM) less potent than spantide. H-D-Arg-Pro-Lys-Pro-Gln-Gln-D-TrpΨ[CH$_2$—H]Phe-D-Trp-Leu-Nle-NH$_2$ was 3.5-times (IC$_{50}$, 6.4-μM) less potent and H-D-Arg-Pro-Lys-Pro-Gln-Gln-D-Trp-PheΨ[CH$_2$—NH]D-Trp-Leu-Nle-NH$_2$ was 17-times (IC50, 30 μM) less potent than spantide (Table 3).

Results for the SP pseudopeptide analogues are shown in FIG. 1, right panel. H-Arg-Pro-Lys-Pro-Gln-Gln-Phe-Phe-Gly- LeuΨ[CH$_2$—NH]Leu-NH$_2$ was the most potent SP derivative causing detectible inhibition at 0.3 μM and half-maximal inhibition at 7.1 μM (Table 3, right). H-Arg-Pro-Lys-Pro-Gln-Gln-Phe-PheΨ[CH$_2$—NH]Gly-Leu- Leu-NH$_2$ and H-Arg-Pro-Lys-Pro-Gln-GlnΨ[CH$_2$—NH]Phe-Phe-Gly-Leu-Leu-NH$_2$ were less effective, causing detectable inhibition at 10 μM. They are, respectively, 7-fold and 46-fold less potent than H-Arg-Pro-Lys-Pro-Gln-Gln-Phe-Phe- Gly-LeuΨ[CH2—NH]Leu-NH$_2$ (Table 3, right). H-Arg-Pro-Lys-Pro-Gln-Gln-PheΨ[CH$_2$-NH]Phe-Gly-Leu-Leu-NH$_2$ exhibited no inhibitory activity at concentrations as high as 30 μM (FIG. 1, right). The most potent SP derived pseudopeptide antagonist was H-Arg-Pro- Lys-Pro-Gln-Gln-Phe-Phe-Gly-LeuΨ[CH₂—NH]Leu-NH₂ (FIG. 1, Table 2).

Figure 2:
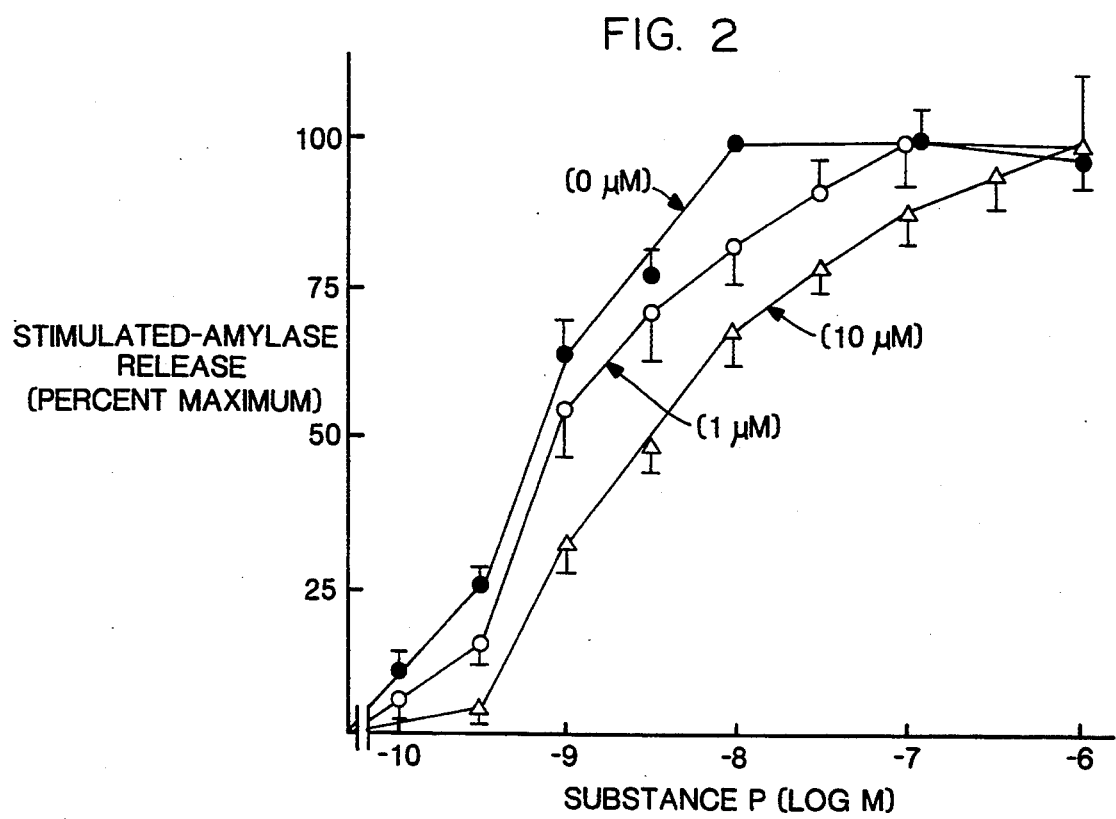
FIG. 2 is a graph showing the effect of H-Arg-Pro-Lys-Pro-Gln-Gln-Phe-Phe-Gly-Leu$\psi$[CH$_2$-NH]Leu-NH$_2$ on SP-stimulated amylase release from pancreatic ancini.

The inhibitory effects of the most potent SP derived pseudopeptide antagonist, Arg-Pro-Lys-Pro-Gln-Gln-Phe-Phe-Gly- LeuΨ[CH₂—NH]Leu-NH₂, are shown in FIG. 2. Acini were incubated with increasing concentrations of SP. Amylase release was detectible with 0.1 nM SP, was half-maximal with 1 nM SP, and was maximal with 10 nM (FIG. 2). Addition of H-Arg-Pro-Lys-Pro-Gln-Gln-Phe-Phe-Gly-LeuΨ[CH₂-NH]Leu-NH₂ caused a parallel rightward shift in the dose-response curve for SP-stimulated amylase release. The shift was proportional to the concentration of H-Arg-Pro-Lys-Pro-Gln-Gln-Phe-Phe-Gly-LeuΨ[CH₂—NH]Leu-NH₂ added but there was no change in the maximal response (FIG. 2). H-D-Arg-Pro-Lys-Pro-Gln-Gln-D-Trp-Phe-D-Trp-LeuΨ[CH₂-NH]Nle-NH₂ gave similar results (data not shown).

The interaction of SP and spantide derived analogues with the SP receptors of pancreatic acini was measured by the ability of a peptide to inhibit the binding of $^{125}$I-BH-SP to acini. (See Table 3 and FIG. 3.)

Figure 3:
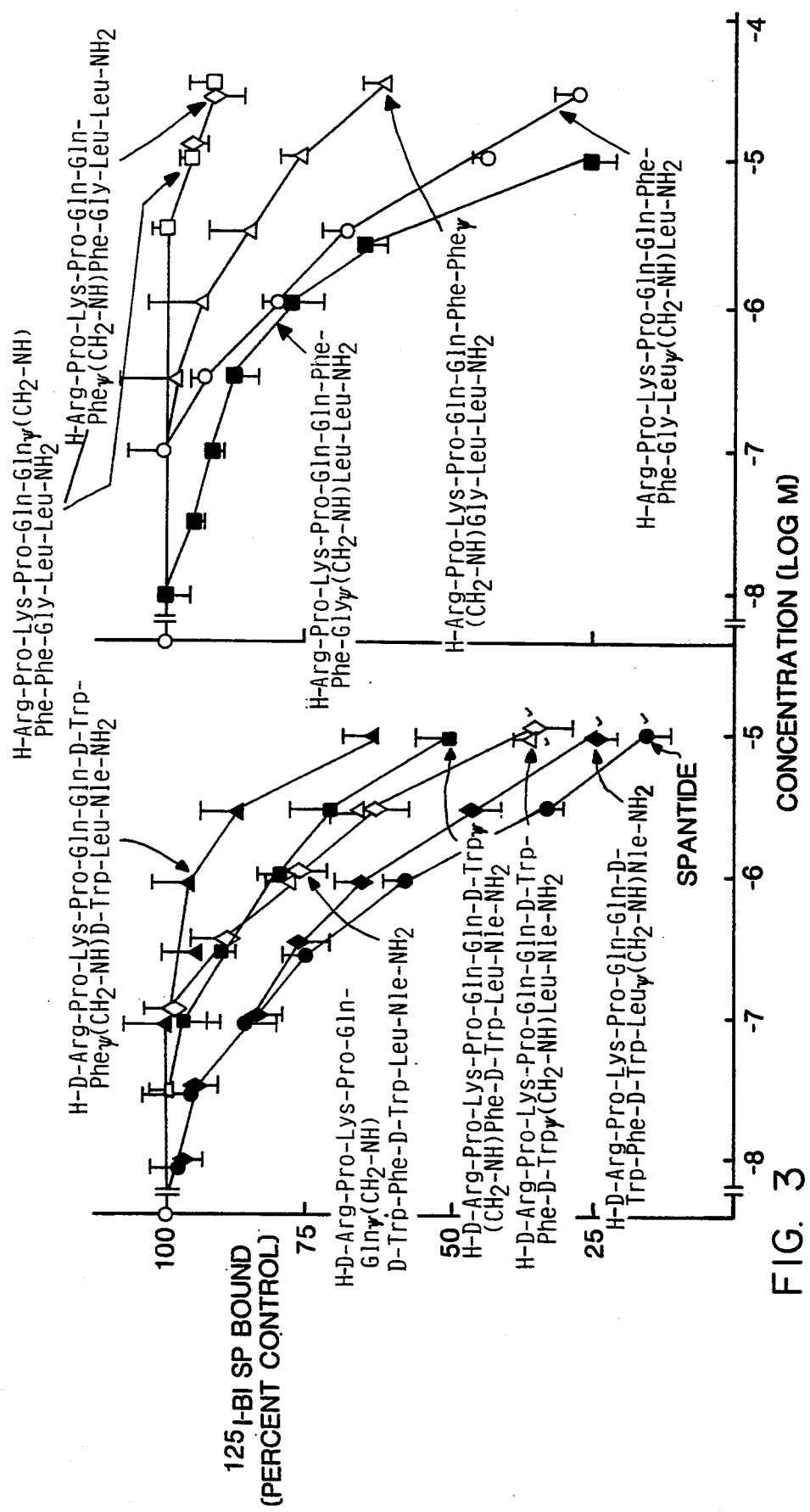
FIG. 3 is a pair of graphs illustrating the ability of various SP and spantide pseudopeptides to inhibit binding of $^{125}$I-BH-substance P to pancreatic ancini.

The spantide derived pseudopeptides show a range of potencies. H-D-Arg-Pro-Lys-Pro-Gln-Gln-D-Trp-Phe-D-Trp-LeuΨ [CH₂NH]Nle-NH₂ is roughly equivalent in potency to spantide causing detectible inhibition at 0.03 μM and half-maximal inhibition at 2.2 μM (FIG. 3, left, Table 3). H-D-Arg-Pro-Lys- Pro-Gln-Gln-D-Trp-Phe-D-TrpΨ[CH₂—NH]Leu-Nle-NH₂ and H-D-Arg-Pro-Lys-Pro-Gln-GlnΨ[CH₂—NH]D-Trp-Phe-D-Trp-Leu-Nle-NH₂ are 2-fold less potent than spantide. H-D-Arg-Pro-Lys-Pro-Gln-Gln-D-TrpΨ[CH₂—NH]Phe-D-Trp-Leu-Nle-NH₂ was 3-times (Ki, 6.3 μM) less potent than spantide. H-D-Arg-Pro-Lys-Pro-Gln-Gln-D-Trp-PheΨ[CH₂—NH]D-Trp-Leu-Nle-NH₂ was 7-times (Ki, 14.7 μM) less potent than spantide (FIG. 3, Table 3).

The SP derived pseudopeptides also show a range of potencies. H-Arg-Pro-Lys-Pro-Gln-Gln-Phe-Phe-Gly-LeuΨ[CH₂—H]Leu-NH₂ causes detectable inhibition at 0.1 μM, and half-maximal inhibition at 3 μM. H-Arg-Pro-Lys-Pro-Gln-Gln-Phe-Phe-GlyΨ[CH₂—NH]Leu-Leu-NH₂ is 1.5-fold lower in potency, H-Arg-Pro-Lys-Pro-Gln-Gln-Phe-PheΨ[CH₂—NH]Gly-Leu-Leu-NH₂ is 20-times less potent, and H-Arg-Pro-Lys-Pro-Gln-Gln-PheΨ[CH₂—NH]Phe-Gly-Leu-Leu-NH₂ and H-Arg-Pro-Lys-Pro-Gln-GlnΨ[CH₂—NH]Phe-Phe-Gly-Leu-Leu-NH₂ are more than 62-times less potent than H-Arg-Pro-Lys-Pro-Gln-Gln-Phe-Phe- Gly-LeuΨ[CH₂—NH]Leu-NH₂.

Unlike previously studied SP analogs the peptides of the invention are specific to the SP receptor. Arg-Pro-Lys-Pro-Gln-Gln-Phe-Phe-Gly-LeuΨ[CH₂—NH]Leu-NH₂ was tested for the ability to inhibit amylase release produced by various pancreatic secretagogues (Table 4). Arg-Pro-Lys-Pro-Gln-Gln-Phe-Phe-Gly-LeuΨ[CH₂—NH]Leu-NH₂ (20 μM) inhibited amylase release stimulated by SP, but did not alter bombesin, CCK-8, carbachol, VIP, secretin, CGRP A23187 or TPA stimulated amylase release.

The most potent receptor antagonists were tested for their ability to inhibit the binding of $^{125}$I-[Tyr$^4$] bombesin to the bombesin receptors of pancreatic acini. Spantide inhibited binding of $^{125}$I-[Tyr$^4$] bombesin as reported previously (Jensen et al. (1988) Am. J. Physiol. 254:G883) causing half-maximal inhibition at 3±1 μM and complete inhibition at 100 μM (FIG. 4). D-Arg-Pro-Lys-Pro-Gln-Gln-D-Trp-Phe-D-Trp-LeuΨ[CH₂—NH] Nle-NH₂ inhibited 125I-[Tyr$^4$] bombesin binding but was 3-fold less potent than spantide causing half-maximal inhibition at 10 μM (p<0.05 compared to spantide) (FIG. 4). Arg-Pro-Lys-Pro-Gln-Gln-Phe-Phe-Gly-LeuΨ[CH₂—NH]Leu-NH₂ did not cause detectable inhibition until concentrations above 30 μM and had a calculated K$_i$ of 300±20 μM. Spantide and H-D-Arg-Pro-Lys-Pro-Gln-Gln-D-Trp-Phe-D-Trp-LeuΨ[CH₂—NH]Nle-NH₂ had a 3- to 10-fold lower affinity for inhibiting $^{125}$I-[Tyr]bombesin binding as compared to $^{125}$I-BH-SP. The ability of H-Arg-Pro-Lys-Pro-Gln-Gln-Phe-Phe-Gly-LeuΨ[CH₂—NH]Leu-NH₂ to inhibit binding of $^{125}$I-[Tyr$^4$] bombesin was 70-fold lower than its ability to inhibit binding of $^{125}$I-BH-SP.

Use

The peptides of the invention may be administered to a mammal, particularly a human, in one of the traditional modes (e.g., orally, parenterally, transdermally, or transmucosally), in a sustained release formulation using a biodegradable biocompatible polymer, or by on-site delivery using micelles, gels and liposomes.

The peptides can be administered to a human patient in a dosage of 0.5 μg/kg/day to 5 mg/kg/day.

TABLE 1

The five carboxyl-terminal residues of a variety of bioactive peptides.

| Peptide | Carboxyl Terminal Sequence |
|---|---|
| Bombesin | —Val—Gly—His—Leu—Met—NH₂ |
| Neuromedin-β | —Thr—Gly—His—Phe—Met—NH₂ |
| Neuromedin-C | —Val—Gly—His—Leu—Met—NH₂ |
| Litorin | —Val—Gly—His—Phe—Met—NH₂ |
| Neurokinin-A | —Phe—Val—Gly—Leu—Leu—NH₂ |
| Neurokinin-B | —Phe—Val—Gly—Leu—Met—NH₂ |
| Substance P | —Phe—Phe—Gly—Leu—Met—NH₂ |
| Prototypical Tachykinin Sequence | —Phe—X—Gly—Leu—Met—NH₂ (where X = a branched aliphatic or aromatic amino acid residue) |

TABLE 2

Effect of the various SP and spantide derived pseudopeptides on basal and SP-stimulated amylase release.

| | Amylase Release (percent total) | |
|---|---|---|
| Peptide Added | Alone | SP (1 nM) |
| None | 3.4 ± 0.5 | 6.6 ± 0.7 |
| H—Arg—Pro—Lys—Pro—Gln—Gln—Phe—Phe—Gly—LeuΨ[CH₂—NH]Leu—NH₂ (10 μM) | 3.1 ± 0.7 | 4.3 ± 0.5* |
| H—Arg—Pro—Lys—Pro—Gln—Gln—Phe—Phe—GlyΨ[CH₂—NH]Leu—Leu—NH₂ (10 μM) | 10.4 ± 1.0** | NT-agonist |
| H—Arg—Pro—Lys—Pro—Gln—Gln—Phe—PheΨ[CH₂—NH]Gly—Leu—Leu—NH₂ (10 μM) | 3.1 ± 1.0 | 5.4 ± 0.7* |
| H—Arg—Pro—Lys—Pro—Gln—Gln—PheΨ[CH₂—NH]Phe—Gly—Leu—Leu—NH₂ (10 μM) | 3.8 ± 0.7 | 6.4 ± 0.3 |
| H—Arg—Pro—Lys—Pro—Gln—GlnΨ[CH₂—NH] | 3.1 ± 0.9 | 6.1 ± 1.0* |

TABLE 2-continued

Effect of the various SP and spantide derived pseudopeptides on basal and SP-stimulated amylase release.

| Peptide Added | Amylase Release (percent total) | |
|---|---|---|
| | Alone | SP (1 nM) |
| Phe—Phe—Gly—Leu—Leu—NH$_2$ (10 μM) H—D—Arg—Pro—Lys—Pro—Gln—Gln—D—Trp—Phe—D—Trp—LeuΨ[CH$_2$—NH]Nle—NH$_2$ (10 μM) | 3.8 ± 0.05 | 3.6 ± 0.1* |
| H—D—Arg—Pro—Lys—Pro—Gln—Gln—D—Trp—Phe—D—TrpΨ[CH$_2$—NH]Leu—Nle—NH$_2$ (10 μM) | 3.9 ± 0.8 | 4.2 ± 0.2* |
| H—D—Arg.Pro—Lys—Pro—Gln—Gln—D—Trp—PheΨ[CH$_2$—NH]D—Trp—Leu—Nle—NH$_2$ (10 μM) | 4.0 ± 0.5 | 5.6 ± 0.8* |
| H—D—Arg—Pro—Lys—Pro—Gln—Gln—D—TrpΨ[CH$_2$—NH]Phe—D—Trp—Leu—Nle—NH$_2$ (10 μM) | 4.1 ± 0.5 | 4.8 ± 1.2* |
| H—D—Arg—Pro—Lys—Pro—Gln—GlnΨ[CH$_2$—NH]D—Trp—Phe—D—Trp—Leu—Nle—NH$_2$ (10 μM) | 3.8 ± 0.3 | 4.5 ± 0.8** |

*Significantly less than SP alone p < 0.05
**Significantly greater than no additions p < 0.01
Acini were incubated at 37° C. for 30 min with 1 nM SP and 10 μM concentrations of the various SP and spantide pseudopeptide analogues either alone or in combination. Amylase release was expressed as percent of amylase activity in acini at the start of incubation that was released into extracellular medium during incubation. Values are means ± 1 SEM from at least 5 separated experiments. In each experiment, each value was determined in duplicate. Abbreviations: NT-agonist = Not tested as an antagonist because it was an agonist.

TABLE 3

Abilities of SP, spantide and pseudopeptide to inhibit binding of $^{125}$I-BH-SP or SP-stimulated amylase release.

| Peptide | $^{125}$I-BH-SP Binding K$_i$ or K$_d$ (μM) | Inhibition of 1nMSP-stimulated Amylase release IC$_{50}$ (μM) |
|---|---|---|
| H—D—Arg—Pro—Lys—Pro—Gln—Gln—D—Trp—Phe—D—Trp—Leu—Leu—NH$_2$ (Spantide) | 2.1 ± 0.6 | 1.8 ± 0.1 |
| H—D—Arg—Pro—Lys—Pro—Gln—Gln—D—Trp—Phe—D—TrpΨ[CH$_2$NH]Nle—NH$_2$ | 2.2 ± 0.4 | 1.8 ± 0.25 |
| H—D—Arg—Pro—Lys—Pro—Gln—Gln—D—Trp—Phe—D—TrpΨ[CH$_2$—NH]Leu—Nle—NH$_2$ | 3.6 ± 0.7 | 3.5 ± 0.6 |
| H—D—Arg—Pro—Lys—Pro—Gln—Gln—D—Trp—PheΨ[CH$_2$—NH]D—Trp—Leu—Nle—NH$_2$ | 14.7 ± 2.0 | 30 ± 5.0 |
| H—D—Arg—Pro—Lys—Pro—Gln—Gln—D—TrpΨ[CH$_2$—NH]Phe—D—Trp—Leu—Nle—NH$_2$ | 6.3 ± 3.3 | 6.4 ± 1.4 |
| H—D—Arg—Pro—Lys—Pro—Gln—GlnΨ[CH$_2$—NH]D—Trp—Phe—D—Trp—Leu—Nle—NH$_2$ | 4.3 ± 1.1 | 4.7 ± 1.3 |
| H—Arg—Pro—Lys—Pro—Gln—Gln—Phe—Phe—Gly—Leu—Met—NH$_2$ (SP) | .0025 ± .0005 | No-Agonist |
| H—Arg—Pro—Lys—Pro—Gln—Gln—Phe—Phe—Gly—LeuΨ[CH$_2$—NH]Leu—NH$_2$ | 4.3 ± 0.3 | 7.1 ± 0.9* |
| H—Arg—Pro—Lys—Pro—Gln—Gln—Phe—Phe—GlyΨ[CH$_2$—NH]Leu—Leu—NH$_2$ | 5.6 ± 2.2 | No-Agonist |
| H—Arg—Pro—Lys—Pro—Gln—Gln—Phe—PheΨ[CH$_2$—NH]Gly—Leu—Leu—NH$_2$ | 41.3 ± 16.7 | >30 |
| H—Arg—Pro—Lys—Pro—Gln—Gln—PheΨ[CH$_2$—NH]Phe—Gly—Leu—Leu—NH$_2$ | 265.0 ± 89.0 | >30 |
| H—Arg—Pro—Lys—Pro—Gln—GlnΨ[CH$_2$—NH]Phe—Phe—Gly—Leu—Leu—NH$_2$ | 310.0 ± 88.0 | >30 |

Values are means ± 1 SEM. Kd values for SP are obtained from Scatchard analysis of $^{125}$I-labeled SP binding studies K$_i$ values for agonist or antagonists from studies of binding $^{125}$I-BH-SP were obtained according to the equation: K$_i$ = (R/1 − R) (SB/S + A) where R is the observed saturable binding of $^{125}$I-BH-SP in the presence of antagonist (B) expressed as a fraction of that obtained when B is not present; A is the concentration of $^{125}$I-BH-SP (0.125 nM). B is the concentration of antagonist, S is the K$_d$ of SP determined by Scatchard analysis. No-agonist = peptide not tested for inhibition activity because agonist activity when present alone.

TABLE 4

Ability of H—Arg—Pro—Lys—Pro—Gln—Gln—Phe—Phe—Gly—LeuΨ[CH$_2$—NH]Leu—NH$_2$ to affect amylase release stimulated by various secretagogues.

| | Amylase Release (percent total) | |
|---|---|---|
| Secretagogue | Alone | Leu$^{11}$, Ψ10-11-SP (20 μM) |
| None | 2.7 ± 0.4 | 2.3 ± 0.3 |
| Substance P (1 nM) | 8.7 ± 1.8 | 4.3 ± 0.5* |
| CCK-8 (0.1 nM) | 19.7 ± 4.2 | 21.6 ± 4.9 |
| Bombesin (0.3 nM) | 14.8 ± 4.1 | 14.3 ± 3.1 |
| Carbachol (10 μM) | 22.7 ± 4.1 | 20.7 ± 4.3 |
| VIP (0.3 nM) | 20.5 ± 3.5 | 18.9 ± 4.2 |
| Secretin (0.1 μM) | 18.9 ± 3.6 | 18.8 ± 4.1 |
| CGRP (0.1 μM) | 12.1 ± 3.3 | 12.0 ± 3.9 |
| A23187 (0.1 μM) | 9.9 ± 1.5 | 11.6 ± 1.6 |

TABLE 4-continued

Ability of
H—Arg—Pro—Lys—Pro—Gln—Gln—Phe—Phe—Gly—
Leu$\Psi$[CH$_2$—NH]Leu—NH$_2$ to affect amylase release stimulated by
various secretagogues.

| Secretagogue | Amylase Release (percent total) | |
|---|---|---|
|  | Alone | Leu$^{11}$, $\Psi$10-11-SP (20 $\mu$M) |
| TPA (0.1 $\mu$M) | 32.2 ± 5.7 | 30.2 ± 5.6 |

*Significantly less than secretagogue alone p < 0.001
Acini were incubated for 30 min at 37° C. with various pancreatic secretagogues alone or with H—Arg—Pro—Lys—Pro—Gln—Gln—Phe—Phe—Gly—Leu$\Psi$[CH$_2$—NH]LeuNH$_2$. In each experiment, each value was determined in duplicate, and results give means ± 1 SEM from at least 4 separated experiments. Abbreviations: CCK-8, COOH-terminal octapeptide of cholecystokinin; VIP, vasoactive intestinal peptide, respectively; CGRP, calcitonin gene-related peptide; A23187 and TPA, 1,2-o-tetradecanoylphorbol-1,3-acetate.

Other embodiments are also within the claims set forth below.

What is claimed is:

1. A substance P analog of the formula:

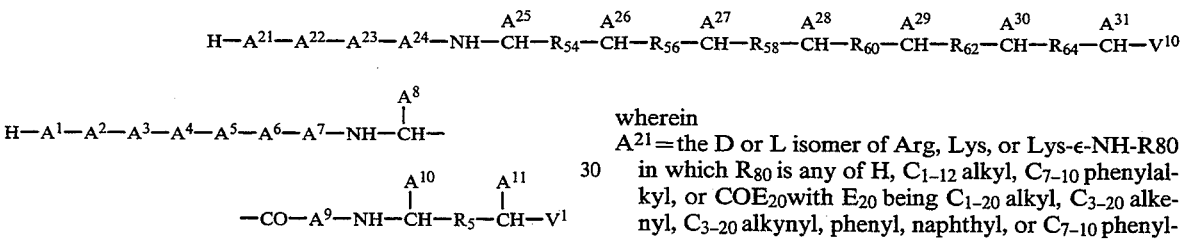

wherein $A^1$ = the D or L isomer of Arg, Lys, or Lys-$\epsilon$-NH-$R_{20}$ in which $R_{20}$ is any of H, $C_{1-12}$ alkyl, $C_{7-10}$ phenylalkyl, or $COE_{10}$ with $E_{10}$ being $C_{1-20}$ alkyl, $C_{3-20}$ alkenyl, $C_{3-20}$ alkynyl, phenyl, naphthyl, or $C_{7-10}$ phenylalkyl; or is deleted;

$A^2$ = the D or L isomer Pro; or is deleted;

$A^3$ = the D or L isomer of Lys, or Lys-$\epsilon$-NH-$R_{22}$ in which $R_{22}$ is any of H, $C_{1-12}$ alkyl, $C_{7-10}$ phenylalkyl, or $COE_{12}$ with $E_{12}$ being $C_{1-20}$ alkyl, $C_{3-20}$ alkenyl, $C_{3-20}$ alkynyl, phenyl, naphthyl, or $C_{7-10}$ phenylalkyl; or is deleted;

$A^4$ = the D or L isomer of Pro; or is deleted;

$A^5$ = the D or L isomer of Asp, Gln, $\beta$-Nal, Trp, Phe, o-X-Phe in which X is F, Cl, Br, NO$_2$, OH, or CH$_3$, or p-X-Phe in which X is F, Cl, Br, NO$_2$, OH, or CH$_3$; or is deleted;

$A^6$ = the D or L isomer of Ala, Arg, Ser, Pro, Gln, p-Glu, Asn, $\beta$-Nal, Trp, Phe, o-X-Phe in which X is F, Cl, Br, NO$_2$, OH, or CH$_3$, or p-X-Phe in which X is F, Cl, Br, NO$_2$, OH, or CH$_3$;

$A^7$ = the D or L isomer of Val, Thr, Phe, Trp, $\beta$-Nal, o-X-Phe in which X is F, Cl, Br, NO$_2$, OH, or CH$_3$, or p-X-Phe in which X is F, Cl, Br, NO$_2$, OH, or CH$_3$;

$A^8$ = the identifying group of Gly or the D or L isomer of Val, Trp, $\beta$-Nal, Phe, o-X-Phe in which X is F, Cl, Br, NO$_2$, OH, or CH$_3$, or p-X-Phe in which X is F, Cl, Br, NO$_2$, OH, or CH$_3$;

$A^9$ = Gly or the D or L isomer of Sar, His, Trp, $\beta$-Nal, Phe, o-X-Phe in which X is F, Cl, Br, NO$_2$, OH, or CH$_3$, or p-X-Phe in which X is F, Cl, Br, NO$_2$, OH, or CH$_3$;

$A^{10}$ = Gly or the identifying group of the D or L isomer of Trp, $\beta$-Nal, Leu, Nle, Ala, cyclohexyl-Ala, Val, Ile, Met, Phe, o-X-Phe in which X is, Cl, Br, NO$_2$, OH, or CH$_3$, or p-X-Phe in which X is F, Cl, Br, NO$_2$, OH, or CH$_3$;

$A^{11}$ = Gly or the identifying group of the D or L isomer of Trp, $\beta$-Nal, Leu, Nle, Ala, Val, Ile, Met, Phe, o-X-Phe in which X is F, Cl, Br, NO$_2$, OH, or CH$_3$, or p-X-Phe in which X is F, Cl, Br, NO$_2$, OH, or CH$_3$; or is deleted;

$R_5$ is $CH_2$—NH and $V^1$ is

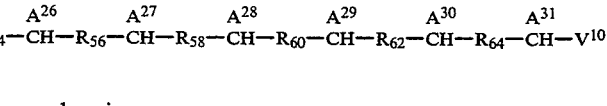

in which each $R_{10}$, $R_{11}$, and $R_{12}$ independently, is H, $C_{1-12}$ alkyl, $C_{7-10}$ phenylalkyl, or $C_{12-20}$ naphthylalkyl; further provided that, where $A^5$ is Asp, $A^6$ is Ser, $A^7$ is Phe, $A^8$ is Val, $A^9$ is Gly, $A^{10}$ is Leu, and $A^{11}$ is Leu, at least one of $A^1$, $A^2$, $A^3$, or $A^4$ must be present; or a pharmaceutically acceptable salt thereof.

2. A substance P analog of the formula:

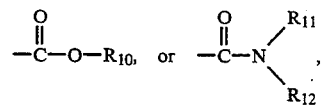

wherein $A^{21}$ = the D or L isomer of Arg, Lys, or Lys-$\epsilon$-NH-$R_{80}$ in which $R_{80}$ is any of H, $C_{1-12}$ alkyl, $C_{7-10}$ phenylalkyl, or $COE_{20}$ with $E_{20}$ being $C_{1-20}$ alkyl, $C_{3-20}$ alkenyl, $C_{3-20}$ alkynyl, phenyl, naphthyl, or $C_{7-10}$ phenylalkyl; or is deleted;

$A^{22}$ = the D or L isomer of Pro; or is deleted;

$A^{23}$ = the D or L isomer of Lys or Lys-$\epsilon$-NH-$R_{82}$ in which $R_{82}$ is any of H, $C_{1-12}$ alkyl, $C_{7-10}$ phenylalkyl, or $COE_{22}$ with $E_{22}$ being $C_{1-20}$ alkyl, $C_{3-20}$ alkenyl, $C_{3-20}$ alkynyl, phenyl, naphthyl, or $C_{7-10}$ phenylalkyl; or is deleted;

$A^{24}$ = the D or L isomer of Pro; or is deleted;

$A^{25}$ = the identifying group of the D or L isomer of Asp, Gln, B-Nal, Trp, Phe, o-X-Phe in which X is F, Cl, Br, NO$_2$, OH, or CH$_3$, or p-X-Phe in which X is F, Cl, Br, NO$_2$, OH, or CH$_3$; or is deleted together with NH—CH bonded thereto;

$A^{26}$ = the identifying group of the D or L isomer of Arg, Sar, Pro, Gln, pGlu, Phe, Trp, cyclohexyl-Ala, or Asn;

$A^{27}$ = the identifying group of D-Trp; or the identifying group of the D or L isomer of Leu, Phe, or cyclohexyl-Ala;

$A^{28}$ = the identifying group of the D or L isomer of any one of the amino acids Val, $\beta$-Nal, Phe, o-X-Phe in which X is F, Cl, Br, NO$_2$, OH, or CH$_3$, or p-X-Phe in which X is F, Cl, Br, NO$_2$, OH, or CH$_3$;

$A^{29}$ = the identifying group of the amino acid D-Trp; or the identifying group of the D or L isomer of any of Leu, Phe, or cyclohexyl-Ala;

$A^{30}$ = the identifying group of the D or L isomer of any one of the amino acids Leu, Nle, Ala, cyclohexyl-Ala, Val, Ile, Met, Gly, Phe, Trp, $\beta$-Nal, o-X-Phe in which X is F, Cl, Br, NO$_2$, OH, or CH$_3$, or p-X-Phe in which X is F, Cl, Br, NO$_2$, OH, or CH$_3$;

$A^{31}$ = the identifying group of the D or L isomer of any one of the amino acids Trp, $\beta$-Nal, Leu, Nle, Ala, Val, Ile, Met, Gly, Phe, o-X-Phe in which X is F, Cl, Br, NO$_2$, OH, or CH$_3$, or p-X-Phe in which X is F, Cl, Br, NO$_2$, OH, or CH$_3$;

$R_{54}$ is CO—NH or CO—NCH$_3$ if A$^{25}$ with NH—CH is not deleted, is NH if A$^{25}$ with NH—CH is deleted; each $R_{56}$, $R_{62}$, and $R_{64}$, independently, is any of CO—NH or CH$_2$—NH; $R_{58}$ is CO—NR$_{69}$ in which $R_{69}$ is H or C$_{1-12}$ alkyl, or CH$_2$—NH; $R_{60}$ is CO—NH; and $V^{10}$ is

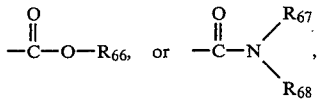

in which each $R_{66}$, $R_{67}$, and $R_{68}$ independently, is H, C$_{1-12}$ alkyl, C$_{7-10}$ phenylalkyl, or C$_{12-20}$ naphthylalkyl; provided that, at least one of $R_{56}$, $R_{58}$, $R_{62}$, or $R_{64}$ is CH$_2$NH; or a pharmaceutically acceptable salt thereof.

3. The substance P analog of claim 1 of the formula: H-Arg-Pro-Lys-Pro-Gln-Gln-Phe-Phe-Gly-LeuΨ[CH$_2$—NH]Leu-NH$_2$; or a pharmaceutically acceptable salt thereof.

4. The substance P analogs of claim 2 of the formula: H-D-Arg-Pro-Lys-Pro-Gln-Gln-D-Trp-Phe-D-TrpΨ[CH$_2$—NH]Leu-Nle-NH$_2$; or a pharmaceutically acceptable salt thereof.

5. The substance P analogs of claim 2 of the formula: H-D-Arg-Pro-Lys-Pro-Gln-Gln-D-Trp-Phe-D-Trp-Leu-Ψ[CH$_2$—NH]Nle-NH$_2$; or a pharmaceutically acceptable salt thereof.

6. The substance P analogs of claim 2 of the formula: H-D-Arg-Pro-Lys-Pro-Gln-Gln-D-Trp-Ψ[CH$_2$—NH]Phe-D-Trp-Leu-Nle-NH$_2$; or a pharmaceutically acceptable salt thereof.

7. The substance P analogs of claim 2 of the formula: H-D-Arg-Pro-Lys-Pro-Gln-Gln-Ψ[CH$_2$—NH]D-Trp-Phe-D-Trp-Leu-Nle-NH$_2$; or a pharmaceutically acceptable salt thereof.

8. The substance P analog of claim 1 in which each A$^1$ through A$^5$ is an amino acid.

9. The substance P analog of claim 2 in which each A$^{21}$ through A$^{25}$ is an amino acid.

* * * * *

UNITED STATES PATENT AND TRADEMARK OFFICE
CERTIFICATE OF CORRECTION

PATENT NO. : 5,410,019          Page 1 of 3
DATED     : April 25, 1995
INVENTOR(S) : David H. Coy, et. al.

It is certified that error appears in the above-indentified patent and that said Letters Patent is hereby corrected as shown below:

Title page, col. 2, Under "OTHER PUBLICATIONS", line 3, replace "Rudingerm" with -- Rudinger--;

Under "OTHER PUBLICATIONS", page 2, col. 1, line 16, replace "Acitivty" with --Activity--;

Under "OTHER PUBLICATIONS", page 2, col. 2, line 1, replace "Develipment" with --Development--;

Under "ABSTRACT", line 3, replace "binding of the peptide" with --binding of said peptide--;

Col. 5, line 53, replace "or is deleted; the D or L isomer Pro; or is deleted;" with --or is deleted; $A^7$ = the D or L isomer Pro; or is deleted; --;

Col. 6, line 30, delete "$R_6$ is C;"

Col. 6, line 39, replace "A" with --$A^6$--;

Col. 6, line 39, replace "$A^6$" with --$A^7$--;

Col. 6, line 40, replace "$A^{10}$" with --$A^{10}$ is Leu--; same line delete "is Leu" (second occurrence);

Col. 7, line 35, delete "Ala" (second occurrence);

UNITED STATES PATENT AND TRADEMARK OFFICE
CERTIFICATE OF CORRECTION

PATENT NO. : 5,410,019
DATED : April 25, 1995
INVENTOR(S) : David H. Coy, et. al.

It is certified that error appears in the above-indentified patent and that said Letters Patent is hereby corrected as shown below:

Col. 7, line 47, replace "$CH_2CH_2$" with --$CH_2$-$CH_2$--; same line, delete "-$CH2$";

Col. 8, line 63, replace "7-amino" with --γ-amino--;

Col. 11, line 60, replace "[Tyr]bombesin" with --[$Tyr^4$]bombesin--;

Col. 12, line 7, replace "Phase 114 Phase 3" with --Phase 1 - Phase 3--;

Col. 12, line 47, replace "[$CH_2$-H]" with --[$CH_2$-NH]--;

Col. 13, line 39, replace "[$CH_2$-H]" with --[$CH_2$-NH]--;

Col. 14, line 14, replace "125I-" with --$^{125}$I- --;

Col. 18, line 23, in the formula, add bonds as shown in red below:

UNITED STATES PATENT AND TRADEMARK OFFICE
CERTIFICATE OF CORRECTION

PATENT NO. : 5,410,019
DATED : April 25, 1995
INVENTOR(S) : David H. Coy, et. al.

It is certified that error appears in the above-indentified patent and that said Letters Patent is hereby corrected as shown below:

$$H-A^{21}-A^{22}-A^{23}-A^{24}-NH-\overset{A^{25}}{\underset{}{C}H}-R_{54}-\overset{A^{26}}{\underset{}{C}H}-R_{56}-\overset{A^{27}}{\underset{}{C}H}-R_{58}-\overset{A^{28}}{\underset{}{C}H}-R_{60}-\overset{A^{29}}{\underset{}{C}H}-R_{62}-\overset{A^{30}}{\underset{}{C}H}-R_{64}-\overset{A^{31}}{\underset{}{C}H}-V^{10}.$$

Signed and Sealed this

First Day of August, 1995

Attest:

BRUCE LEHMAN

Attesting Officer        Commissioner of Patents and Trademarks